128/660

United States Patent [19]

Kawabuchi et al.

[11] Patent Number: 4,699,150

[45] Date of Patent: Oct. 13, 1987

[54] ULTRASONIC TRANSDUCER ASSEMBLY FOR MEDICAL DIAGNOSTIC EXAMINATIONS

[75] Inventors: Masami Kawabuchi, Yokohama; Koji Matsuo, Tokyo; Fumio Muramatsu, Atsugi; Akira Fukumoto, Tokyo; Koetsu Saito, Sagamihara, all of Japan

[73] Assignee: Matsushita Electric Industrial Co., Ltd., Japan

[21] Appl. No.: 864,563

[22] Filed: May 16, 1986

Related U.S. Application Data

[63] Continuation of Ser. No. 618,367, Jun. 7, 1984, abandoned.

[30] Foreign Application Priority Data

Jun. 7, 1983 [JP] Japan ............ 58-102025

[51] Int. Cl.⁴ ............ A61B 10/00

[52] U.S. Cl. ............ 128/660; 73/644

[58] Field of Search ............ 128/660–663; 73/632, 644; 310/335; 524/413

[56] References Cited

U.S. PATENT DOCUMENTS

| | | | |
|---|---|---|---|
| 3,269,173 | 8/1966 | Ardenne | 128/660 |
| 3,387,604 | 6/1968 | Erikson | 310/335 |
| 3,958,559 | 5/1976 | Glenn et al. | 128/660 |
| 4,001,766 | 1/1977 | Hurwitz | 310/335 |
| 4,078,435 | 3/1978 | Kossoff et al. | 128/660 |
| 4,121,468 | 10/1978 | Glover et al. | 128/660 |
| 4,143,554 | 3/1979 | Nagy et al. | 73/644 |
| 4,197,921 | 4/1980 | Alphonse et al. | |
| 4,205,686 | 6/1980 | Harris et al. | 128/660 |
| 4,281,550 | 8/1981 | Erikson | 128/660 |
| 4,316,271 | 2/1982 | Evert | 128/660 |
| 4,385,255 | 5/1983 | Yamaguchi et al. | 310/335 |
| 4,387,720 | 6/1983 | Miller | 73/644 |
| 4,440,025 | 4/1984 | Hayakawa et al. | 128/660 |
| 4,471,084 | 9/1984 | Kuwahata et al. | 524/413 |

*Primary Examiner*—Kyle L. Howell
*Assistant Examiner*—Ruth S. Smith
*Attorney, Agent, or Firm*—Lowe, Price, LeBlanc, Becker & Shur

[57] ABSTRACT

An ultrasonic transducer for medical diagnostic examinations which comprises a transducer element having one surface through ultrasonic waves are emitted, an acoustic impedance matcher, and a contact member brought to contact with an object being examined and formed on the one surface of the ultrasonic transducer element. The contact member includes at least a flat plate or an acoustic lens made of a-4-methylpentene-1-base polymer which has high mechanical strength. Transducer arrays and assemblies using such polymer as a member directly contacted with human body are also described.

1 Claim, 14 Drawing Figures

ULTRASONIC TRANSDUCER ASSEMBLY FOR MEDICAL DIAGNOSTIC EXAMINATIONS

This application is a continuation of application Ser. No. 618,367, filed June 7, 1984, now abandoned.

BACKGROUND OF THE INVENTION

1. Field of the Invention

This invention relates to ultrasonic transducers for use in ultrasonic diagnostic systems and more particularly, to the use of a specific type of polymer material for reinforcement of the transducer.

2. Description of the Prior Art

In the medical fields, ultrasonic diagnostic systems have been widely used in recent years. The ultrasonic diagnostic systems make use of a variety of ultrasonic transducers. Typical ultrasonic transducers are illustraed with reference to FIGS. 1(*a*) through 1(*c*) in which they are schematically shown.

Ultrasonic transducers shown in FIGS. 1(*a*) and 1(*b*) are of the single element type. In the figures, reference numerals 1, 2 indicate electrodes attached to a piezoelectric ceramic material 3 on opposite sides thereof, thereby giving a transducer element 4. The electrodes 1 and 2 have lead wires 5 and 6, respectively. On the electrode 2 is formed an acoustic impedance matcher 7 made of one or more layers. This matcher 7 serves to transmit an ultrasonic wave generated from the transducer element 4 in order to improve energy transfer between the high impedance piezoelectric ceramic material and the low impedance of human body being examined as is known in the art. The matcher 7 has an acoustic lens 8 on the side opposite to the electrode 2, by which the ultrasonic wave propagated through the acoustic impedance matcher 7 is focused and transmitted to the object being examined with an improved lateral resolution. In FIG. 1(*a*), a damping member 11 is provided in order to mechanically damp the transducer element 4 therewith.

FIG. 1(*c*) shows a linear transducer array. In this array, a multiplicity of transducer elements, e.g. several tens to several hundreds of elements, are linearly arranged on a plane.

The ultrasonic transducers having such constructions as described above are brought to contact with an object being examined at one surface of the acoustic lens 8 so as to transmit and receive ultrasonic waves, thereby diagnostically examining the object.

The acoustic impedance matcher 7 of the known ultrasonic transducers is usually constituted of one layer of a mixture of metal powder and a resin, or two layers including a first layer of glass and a second layer of plastic resin, with a thickness of as small as 0.2 to 0.5 mm. The acoustic lens 8 is made, for example, of silicone rubber and has a thickness as small as 0.5 to 1 mm. One of disadvantages of the known transducers is that they are low in mechanical strength as a whole and especially, the portion which is brought to direct contact with an object being examined is low in mechanical strength. Although the ultrasonic transducer having the construction shown in FIG. 1(*a*) is improved in mechanical strength over those transducers of FIGS. 1(*b*) and 1(*c*), it has the drawback that its sensitivity lowers by 4 to 10 dB.

In certain transducers having constructions similar to those shown in FIGS. 1(*a*) through 1(*c*), a protective rubber or resin film is further provided on the side of the acoustic lens 8 which is directly contacted with an object being examined, or between the acoustic lens 8 and the acoustic impedance matcher 7. However, the rubber or resin materials are not favorable from the standpoint of acoustic characteristics: an acoustic impedance thereof is not suitable, acoustic waves attenuate considerably, and/or sensitivity and ring down characteristic lower considerably.

On the other hand, there is known a mechanical scanner-type ultrasonic transducer assembly which comprises an ultrasonic transducer of the construction of FIG. 1(*a*) or 1(*b*) encased in a container having an acoustic window. In the container is filled a nearby fluid such as degassed water. In operation, the ultrasonic transducer is mechanically swung so that an object being examined is sector scanned. In this case, the acoustic window which is directly contacted with the object is one of the most important parts of the assembly. The acoustic window must have an acoustic impedance similar to or near the acoustic impedance of the human body (i.e. 1.5 to $1.7\times10^5$ g/cm$^2$S) and a reduced degree of acoustic wave attenuation with high mechanical strength. This window is usually made of polyethylene which has an acoustic impedance of $2.3\times10^5$ g/cm$^2$S and an acoustic wave attenuation as large as about 1 dB/mm/MHz. The mechanical hardness is as low as about 90 as expressed by Shore hardness A. Thus, the acoustic characteristics and mechanical reliability are not necessarily satisfactory.

SUMMARY OF THE INVENTION

It is an object of the invention to provide ultrasonic transducer assemblies which include a member made of a specific type of polymer material.

According to one embodiment of the invention, an ultrasonic transducer comprises a transducer element having one surface through which ultrasonic waves are emitted, an acoustic impedance matcher having a thickness of a quarter wavelength formed on the one surface of the transducer element, and a contact member which is brought to contact with an object being examined and formed on the one surface of the ultrasonic transducer element, the contact member being made of a 4-methylpenten-1-base polymer of high mechanical strength. The contact member may be in the form of a thin flat plate by which a transducer of the non-focussing type is obtained. On the other hand, the contact member may be in the form of a plano-concave form. By this, the transducer obtained is of the focussing type. In the latter case, the contact member serves also as an acoustic lens. Alternatively, the contact member may be constituted of an integral combination of an acoustic lens made of silicone rubber and a reinforcement of a 4-methylpentene-1-base polymer. The acoustic lens and the reinforcement may be formed on the matcher in this or reversed order.

According to another embodiment of the invention, a transducer array is also provided in which a multiplicity of transducer elements are arranged on a flat or spherically curved surface so that they are acoustically separated from one another. On the flat or spherically curved surface are formed an acoustic impedance matcher and a contact member in the same manner as described with reference to the first embodiment.

A further embodiment of the invention comprises a container having an acoustic window made of 4-methylpentene-1-base polymer through which an ultrasound wave generated from an ultrasonic transducer is transmitted and received. An acoustic wave transfer medium such as degassed water is filled in the container. The acoustic window is contacted with an object being examined.

DETAILED DESCRIPTION AND EMBODIMENTS OF THE INVENTION

Figure 1A:
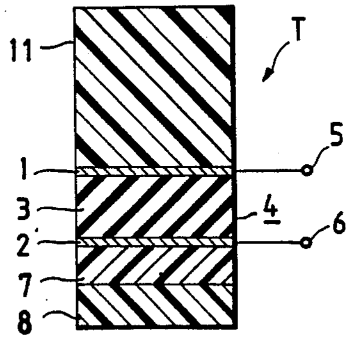
FIG. 1a PRIOR ART
FIGS. 1(*a*) through 1(*c*) are schematic sectional views of known ultrasonic transducers, respectively.

Reference is now made to the accompanying drawings, in which like reference numerals indicate like parts, and particularly to FIGS. 2(*a*) through 2(*f*). FIGS. 2(*a*) through 2(*f*) show single element types of ultrasonic transducers according to the invention. In FIG. 2(*a*), there is shown transducer 10 of a non-focussing type which includes, similar to FIGS. 1(*a*) through 1(*c*), electrodes 11, 12 having lead wires 15, 16, respectively, and a piezoelectric ceramic material 13 interposed between the electrodes 11, 12, thereby giving a transducer element 14. On the electrode 12 are formed an acoustic impedance matcher 17 and a contact member 18. The contact member 18 is brought to direct contact with an object being examined (not shown), e.g. a human body. The acoustic impedance matcher 17 is made of glass, synthetic resins and the like as is well known in the art and may be constituted of a single layer or two or more layers. The thickness of the matcher 17 is an about quarter wavelength of an acoustic wave passing through the acoustic impedance matcher 17 as usual.

The contact member 18 is made of 4-methylpentene-1-base polymer and has generally a thickness of from 1 to 5 mm. The 4-methylpentene-1-base polymer is a kind of a polyolefin. 4-Methylpentene-1 is a dimer of propylene. The term '4-methylpentene-1-base polymer' means methylpentene homopolymer, or copolymers of 4-methylpentene-1 with olefinic monomers such as ethylene, propylene, butylene and higher olefins, and will be hereinafter referred to simply as polymethylpentene. The methylpentene homopolymer has recurring units of the formula $$-(\underset{\substack{| \\ CH_2 \\ | \\ CH(CH_3)_2}}{CH}-CH_2)_n-$$

The polymethylpentene is prepared according to known techniques for ordinary olefins and is commercially available, for example, from Mitsui Petrochemical Industries, Limited under the designations of RT 18, DX 810, MX 004 and MX 221M. Such a polymer usually has an acoustic impedance ranging from 1.46 to $1.70\times10^5$ g/cm$^2$.S at temperatures of from 25° to 37° C., which is thus very close or equal to an acoustic impedance of the human body of $1.54\times10^5$ g/cm$^2$.S. The polymethylpentene has the following physical characteristics: initial flexural modulus of 7,500 to 24,000 kg/cm$^2$, Charpy impact strength of 4 to 5 kg.cm/cm$^2$, Izod impact strength of 10 to 50 kg.cm/cm, Shore hardness of 100, and Rockwell hardness of 60 to 90.

In the above embodiment, the contact member 18 is illustrated as flat on both surfaces thereof. However, the contact member 18 may have a plano-concave form as particularly shown in FIG. 2(*b*). This arrangement makes use of a polymethylpentene acoustic lens serving also as a reinforcement. The reason why the lens is in the plano-concave form is that polymethylpentene which has a sound velocity of 2000 m/second has to be shaped in plano-concave form in order that ultrasound waves are suitably focussed in a human body being examined. In general, the shape of an acoustic lens depends on the ratio of a sound velocity in an acoustic lens to a sound velocity in human body. Silicone rubber ordinarily used as an acoustic lens has a sound velocity of about 1000 m/second and thus should be shaped in plano-convex or biconvex form.

The contact member made of poymethylpentene is described above. Alternatively, the contact member 18 may be made of a combination of a reinforcement 18*a* and an acoustic lens 18*b* as shown in FIGS. 2(*c*) and 2(*d*). In this case, the acoustic lens 18*b* is made of silicone rubber and has a plano-convex form. The reinforcement 18*a* is made of the polymethylpentene which is high in mechanical strength.

The transducers of the single element type may further include a damping member 19 as particularly shown in FIG. 2(*d*). The damping member 19 is usually made of synthetic resins dispersing therein metal powder such as tungsten, ferrites or the like.

In FIGS. 2(*c*) and 2(*d*), the acoustic lens 18*b* is depicted as a plano-convex lens but may have, as shown in FIG. 2(*e*), a biconvex form 18*b*' in which case the reinforcement 18*a*' is in a plano-concave form to permit integral combination with the biconvex lens.

In order to further improve the surface strength of transducer, it is preferably to form, on the acoustic impedance matcher 17, an acoustic lens 18*b*' and a reinforcement 18*a*' in this order as shown in FIG. 2(*f*). More particularly, the contact member 18 is made of the plano-convex lens 18*b*' formed on the acoustic impedance matcher 17. The reinforcement 18*a*' of the plano-convex form is further formed to fully cover the plano-convex lens 18*b*' therewith. In this connection, the plane or flat surface of the lens 18*b*' may be curved depending on an intended ratio of the total of a sound velocity in the acoustic lens 18*b*' and a sound velocity in the reinforcement 18*a*' to a sound velocity in an object being examined. The contact member arrangement of FIG. 2(*f*) in which the reinforcement 18*a*' is formed as the outermost layer, the transducer is noticeably improved in impact strength, wear resistance, scratch resistance and the like, with acoustic characteristics not lowering.

Figure 3A:
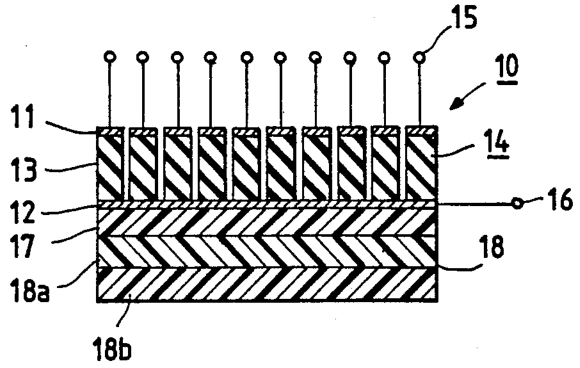
FIGS. 3(*a*) and 3(*b*) are schematic sectional views showing linear or curved array transducers according to another embodiment of the invention.
Figure 3B:
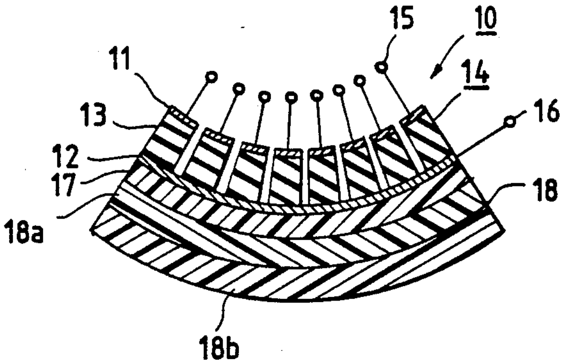

FIG. 3(*a*) shows a linear array transducer 10 including a multiplicity of transducer elements 14 which are acoustically separated from one another and are arranged linearly. On a common electrode 12' are formed the acoustic impedance matcher 17 and the contact member 18. The contact member 18 is depicted as a combination of the reinforcement 18*a* and the acoustic lens 18*b*, but may have such arrangements as illustrated with reference to FIGS. 2(*a*), 2(*b*), 2(*e*) and 2(*f*). The multiplicity of transducer elements 14 may be arranged on a spherically curved common electrode 12 in such a way that axes of the individual transducer elements are extended outwardly and radially of the spherically curved surface. This is particularly shown in FIG. 3(*b*).

Figure 1B:
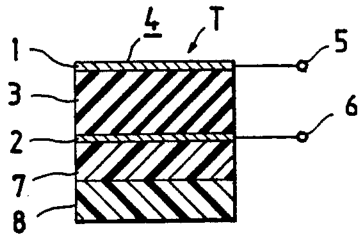
FIG. 1b PRIOR ART
Figure 1C:
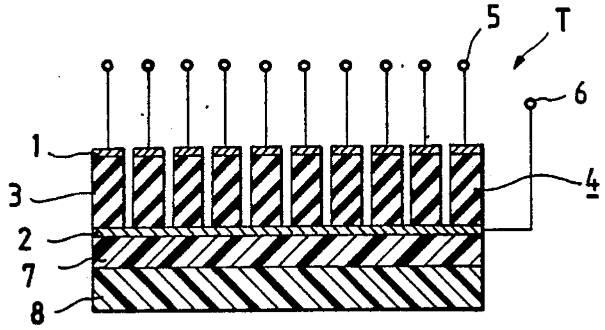
FIG. 1c PRIOR ART
Figure 2A:
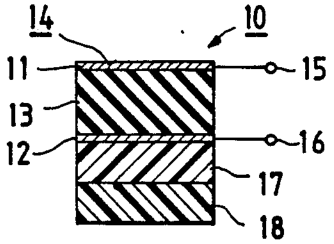
FIGS. 2(*a*) through 2(*f*) are schematic sectional views showing ultrasonic transducers of the single element types according to one embodiment of the invention.
Figure 2B:
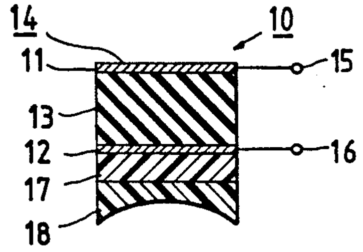
Figure 2C:
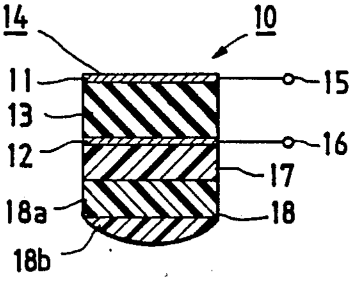
Figure 2D:
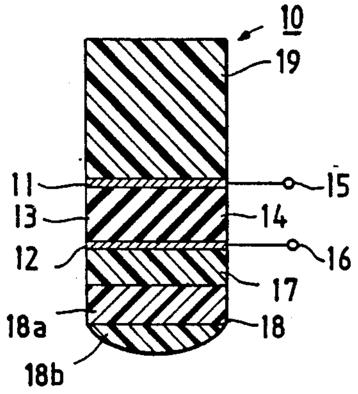
Figure 2E:
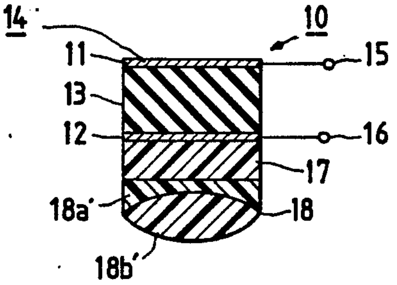
Figure 2F:
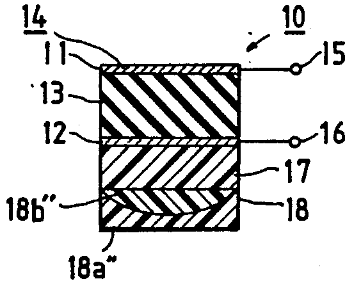

When, for instance, acoustic transducers or arrays thereof are so constructed as shown in FIGS. 2(*a*) through 2(*f*) and 3(*a*) and 3(*b*) are subjected to the falling ball impact test in which a steel ball of 5 g in weight is dropped on the contact member 18, it will be seen that impact strength is at least 100 times as high as the impact strength of the known acoustic transducers shown in FIGS. 1(*a*) through 1(*c*).

The transducers using the polymethylpentene member are notl so changed with respect to the attenuation of ultrasonic wave: an attenuation only by 0.27 dB per unit thickness by mm occurs at a frequency of 3.5 MHz.

Figure 4:
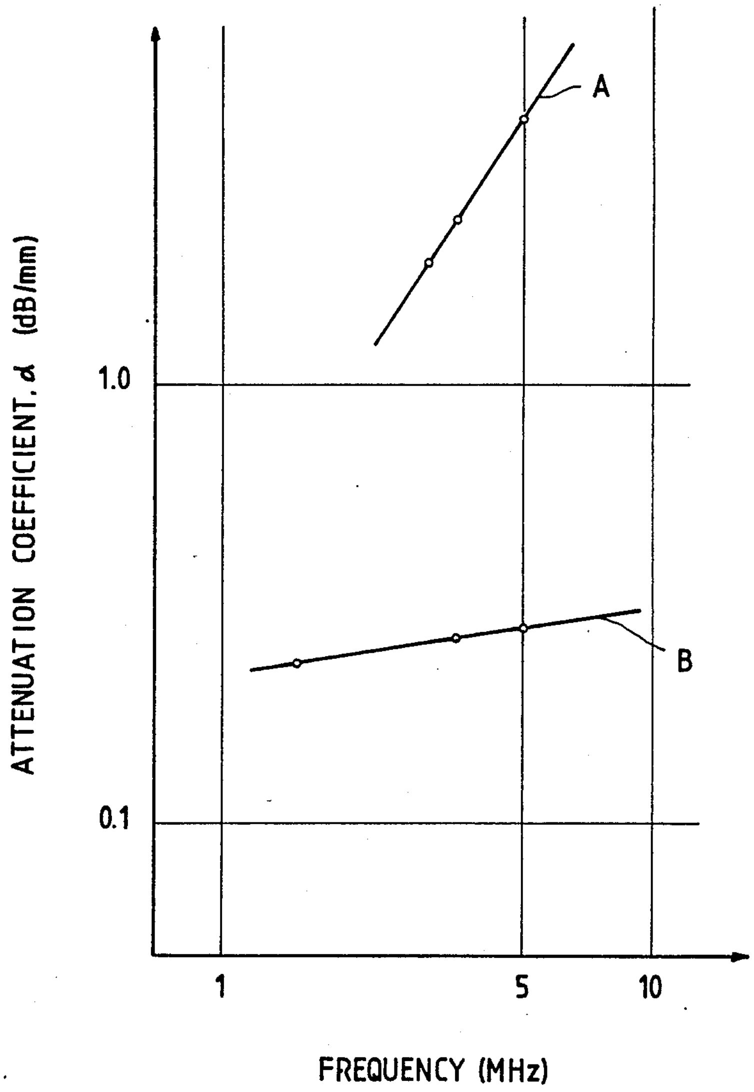
FIG. 4 is a graphic representation of the relation between acoustic wave attenuation and frequency of polymethylpentene.

The dependence of the ultrasonic wave attenuation on the frequency is very small. For instance, upon comparing with an acoustic transducer using a silicone rubber reinforcing plate, the transducer of the invention in which polymethylpentene is used as the contact member is smaller in frequency dependence of the acoustic wave attenuation with a smaller absolute value. This is particularly shown in FIG. 4 in which line A is for silicone rubber and line B is for polymethylpentene.

In the foregoing embodiments, polymethylpentene is used in direct association with the acoustic impedance matcher. This polymer which has excellent acoustic and mechanical properties may be effectively used as a contact member which is provided at a distance from a transducer.

Figure 5:
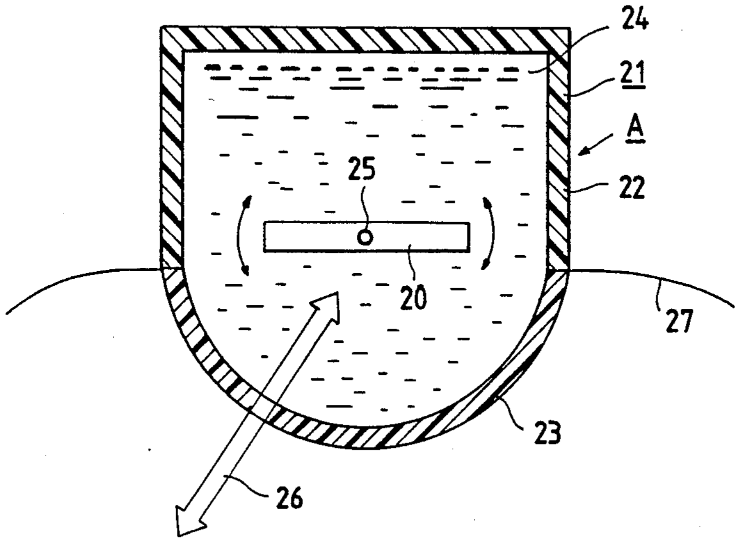
FIG. 5 is a schematic sectional view of an ultrasonic transducer assembly of the mechanical scan type according to a further embodiment of the invention.

One such ultrasonic transducer assembly A is shown in FIG. 5 in which reference numeral 20 designates an ultrasonic transducer of, for example, the known type shown in FIGS. 1(*a*) and 1(*b*). This transducer 20 is encased in a container 21 which includes a casing 22 and an acoustic window 23 of the semi-circular form. In the container 21 is filled a nearby or acoustic wave transfer medium 24 such as degassed water. The ultrasonic transducer 20 in the container 21 is so arranged that it is mechanically swung by means of a shaft 25 rotated by a motor (not shown) in directions indicated by arrows by which ultrasonic waves 26 are transmitted toward and received from an object or human body being examined 27 by a sector scan technique. The acoustic window 23 serving as a contact member is made of polymethylpentene. In prior art sector scan-type transducer assemblies, it is usual to use polyethylene as the acoustic window. Polymethylpentene has an acoustic impedance very close·or equal to the nearby fluid 24 and the object 27. As compared with the acoustic polyethylene window, the acoustic window of the polymer of the invention is more reduced in multipath reflection between the ultrasonic transduer 20 and the acoustic window 23 and also in acoustic wave attenuation in the acoustic window 23. Because of the high mechanical strength, even when the window 23 is pressed against the object 27, its degree of deformation is very small.

Although FIG. 5 shows the mechanical sector scan-type ultrasonic transducer assembly in which the single element type ultrasonic transducer is swung in opposite directions at high speed, polymethylpentene polymer may be also applied as an acoustic window of a mechanical linear scan-type ultrasonic transducer assembly. This type of assembly has a construction similar to the construction of FIG. 5 but in which the transducer is secured to a moving means and is mechanically moved in opposite directions along a strain or curved path by a pulse motor or DC motor.

Figure 6:
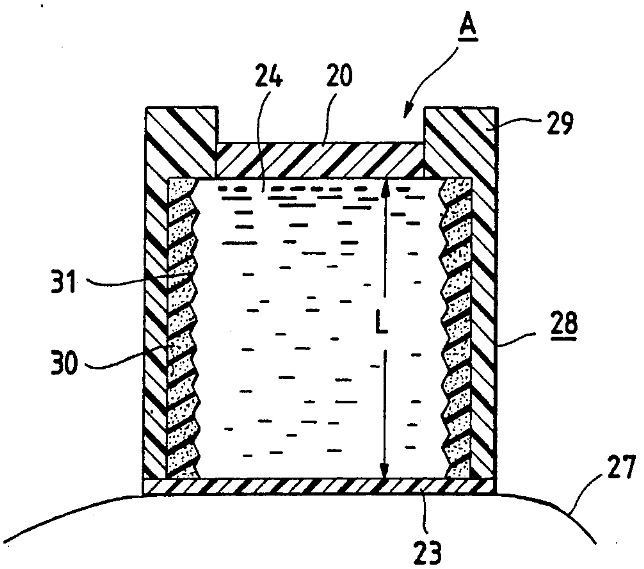
FIG. 6 is a schematic sectional view of an ultrasonic transducer assembly having an acoustic wave coupler according to the invention.

FIG. 6 shows a further embodiment in which an ultrasonic transducer assembly A different from the construction of the assembly of FIG. 5 is shown. The single element type ultrasonic transducer 20 is detachably combined with an acoustic wave coupler 28 as shown. The coupler 28 is constituted of a casing 29 and an acoustic window 23 of a flat plate form. On the inner side walls of the casing 29 is lined an acoustic wave absorber 30 made of rubber having a multiplicity of fins 31. An acoustic wave transfer fluid 24 is filled in the casing 29. The acoustic window 23 is made of polymethylpentene. If necessary, the casing 29 may be also made of polymethylpentene but is usually made of other polyolefins.

In operation, acoustic waves generated from the transducer 20 are passed through the fluid 24 and the acoustic window 23 to the object 27 being examined. A distance between the transducer 20 and the object 27 is suitably controlled by controlling a length, L, of the coupler 28 by which the ultrasonic beam can be focussed to a desired position of the object 27. The acoustic window 23 serves as a contact member and is brought to contact with the object. The window 23 is made of polymethylpentene, so that the assembly is much improved in mechanical strength without a loss of acoustic characteristics.

What is claimed is:

1. An ultrasonic transducer assembly for use in medical diagnostic examinations comprising (a) an ultrasonic transducer member having (i) a transducer element with one surface through which an ultrasonic wave is emitted, (ii) an acoustic impedance matcher formed on the one surface, and (iii) an acoustic lens formed on said acoustic impedance matcher, (b) means for rotationally moving said ultrasonic transducer member, (c) a casing having an acoustic window of a semi-circular form in section and a uniform thickness and encasing said ultrasonic transducer member therein, and (d) an acoustic wave transfer liquid filling said casing, said acoustic window being adapted to contact an object being examined and consisting of a 4-methylpentene-1-base polymer selected from the group consisting of methylpentene homopolymer and copolymers of 4-methylpentene-1 with an olefinic manner, wherein said polymer has an initial flexural modulus of 7,500 to 24,000 kg/cm$^2$, a Charpy impact strength of 4 to 5 kg.cm/cm$^2$, an Izod impact strength of 10 to 50 kg.cm/cm, a Shore hardness of 100, and a Rockwell hardness of 60 to 90.

* * * * *